US005523083A

United States Patent [19]
Shasha et al.

[11] Patent Number: 5,523,083
[45] Date of Patent: Jun. 4, 1996

[54] SPRAYABALE GLUTEN-BASED FORMULATION FOR PEST CONTROL

[75] Inventors: Baruch Shasha, Peoria; Michael McGuire, Metamora, both of Ill.

[73] Assignees: The United States of America as represented by the Secretary of Agriculture, Washington, D.C.; Biotechnology Research and Development Corporation, Peoria, Ill.

[21] Appl. No.: 353,918

[22] Filed: Dec. 12, 1994

Related U.S. Application Data

[63] Continuation-in-part of Ser. No. 134,999, Oct. 11, 1993, abandoned.

[51] Int. Cl.$^6$ .......................... A01N 25/00; A01N 25/24; C12N 1/00
[52] U.S. Cl. ..................... 424/93.1; 424/195.1; 424/405; 424/407
[58] Field of Search .............................. 424/195.1, 405, 424/407, 93.1

[56] References Cited

U.S. PATENT DOCUMENTS

| | | | |
|---|---|---|---|
| 3,111,416 | 11/1963 | Gaver | 106/146 |
| 3,607,370 | 9/1971 | Aranyi et al. | 117/122 P |
| 3,891,756 | 6/1975 | Kasugai et al. | 424/177 |
| 4,230,687 | 10/1980 | Sair et al. | 424/22 |
| 4,841,669 | 6/1989 | Demarest et al. | 43/131 |
| 5,012,004 | 4/1991 | Takahashi et al. | 568/53 |
| 5,055,491 | 10/1991 | Yano et al. | 514/531 |
| 5,057,141 | 10/1991 | Rodriquez-Kabana | 71/28 |
| 5,074,902 | 12/1991 | Connick Jr. et al. | 71/79 |
| 5,091,183 | 2/1992 | Yano et al. | 424/405 |
| 5,135,744 | 8/1992 | Alexander et al. | 424/78.17 |
| 5,238,060 | 2/1994 | Shieh | 424/93 L |
| 5,290,749 | 3/1994 | Christians et al. | 504/189 |
| 5,290,757 | 3/1994 | Christians et al. | 504/355 |
| 5,358,863 | 10/1994 | Quimby, Jr. et al. | 435/178 |

FOREIGN PATENT DOCUMENTS 0301278   2/1989   European Pat. Off. .

OTHER PUBLICATIONS

Chung, O. K., *Cereal Foods World*, 31:242–256 (1986).
*The Merck Index 11th ed.*, Merck & Co., Inc., Rahway, N.J., 1989, pp. 703, 966, 1113, 709, 1523, 495, 895, 472, 269, 270, 441.
Dunkle, R. L., and Shasha, B. S., *Environ. Entomol.* 17:120–126 (1988).
Hughes, P. R., and Wood, H. A., *J. Invertebr. Pathol.* 37:154–159 (1981).
Koestler, R. C., Microencapsulation by interfacial polymerization techniques–agricultural applications, pp. 117–132. In A. F. Kydonieus [ed.] Controlled release technologies: methods, theory, and applications. CRC Press, Boca Raton (1981).
Krull, L. H. and Inglett, G. E., *Cereal Science Today*, 16:232–236 (1971).
Krull, L. H. and Wall, J. S., *Canadian J. of Biochemistry*, 47:581–585 (1969).
Lampman, R. L. and Metcalf, R. L., *Environ. Entomol.* 17:644–648 (1988).
Lance, D. R., *J. Chem. Ecol.* 14:1177–1185 (1988).
Lance, D. R., and Sutter, G. R., *J. Econ. Entomol.* 83:1085–1090 (1990).
Magnuson, K. M., *Cereal Foods World*, 30:179–181 (1985).
McGuire et al., *J. Econ. Entomol.* 84:1652–1656 (1991).
McGuire M. R. and Shasha, B. S., *J. of Econ. Entomol.* 83:1813–1817 (1990).
Meinke et al. *J. Econ. Entomol.* 82:1830–1835 (1989).
Raun et al., *J. of Econ. Entamal.* 59:620–622 (1966).
Shasha et al., *J. Appl. Polym. Sci.* 29:67–73 (1984).
Shasha, B. S. & M. R. McGuire. Slow release formulations of pesticides. In D. G. Chasin & L. E. Bode, (eds), Pesticide formulations and application systems. American Society of Testing and Materials, Philadelphia (1991).
Shaw et al., *J. Econ. Entomol.* 77:1495–1499 (1984).
Trimnell et al., "pesticide Encapsulation Using a Starch–Borate Complex as Wall Material," *J. of Applied Polymer Science, 27:3919–3928 (1982).*
Trimnell, D. and Shasha, B. S., *J. Controlled Release* 7:263–268 (1988).
Synek, J., Formulation, development and application of an insecticide granule, pp. 123–131. In T. M. Kaneko & N. B. Akesson [eds.] Pesticide formulations and application systems: third symposium, ASTM STP 828. American Society for Testing and Materials, Philadelphia, (1983).
Vander Hooven, D. I. B., Corncob granules and pelleted carriers–new, controlled, safer methods of handling pesticides, pp. 132–140. In T. M. Kaneko & N. B. Akesson [eds.] Pesticide formulations and application systems: third symposium, ASTM STP 828. American Society for Testing and Materials, Philadelphia, 1983.
Wall et al., *J. Polymer Sci.*, 24:147–161 (1968).
Wall, J. S. and Beckwith, A. C., *Ceraal Science Today*, 14:2455 (1969).
Wall, J. S. and Huebner, F. R., *Protein Functionality in Foods* 147:110–130 (1980).
Weissling, T. J. & Meinke, L. J., *J. Econ Entomol.* 84:601–609 (1991).
Wing, R. E. and Otey, T. H., *J. Polym. Sci. Polym. Sci. Polym. Chem. Ed.* 21:121–140 (1983).
Huebner et al., "Fractionation and Quantitative Differences of Glutenin from Wheat Varieties Varying in Baking Quality," *Cereal Chemistry*, 53(2):258–269 (1976).

*Primary Examiner*—Michael G. Wityshyn
*Assistant Examiner*—Kristin K. Larson
*Attorney, Agent, or Firm*—Arnold, White & Durkee

[57] ABSTRACT

The present invention provides a process of formulating a pest control agent into a sprayable gluten-based formulation. A gluten-based formulation for use in pest control is also provided. The present invention also provides a process of decreasing the population of a pest of a living organism comprising formulating a pest control agent into a sprayable gluten-based formulation and delivering the formulation to the external surface of the living organism.

23 Claims, No Drawings

SPRAYABALE GLUTEN-BASED FORMULATION FOR PEST CONTROL

CROSS REFERENCE TO RELATED APPLICATIONS

This application is a continuation-in-part of patent application Ser. No. 08/134,999, filed Oct. 11, 1993, now abandoned.

TECHNICAL FIELD OF THE INVENTION

The present invention relates to a sprayable gluten-based formulation, a process of incorporating a biological or chemical substance such as a pest control agent into such a formulation and the use of such a formulation to decrease the population of a pest of a living organism.

BACKGROUND OF THE INVENTION

Myriad approaches have been pursued to control pests. Many of these methods and compositions are directed to control of pests that attack plants, most notably commercially valuable plants. Although much current agricultural research has pest control as its objective, pest destruction of plants and plant products is still a major problem.

Control of pests of plants, livestock, and households has been accomplished with the aid of chemical and biological control agents. Unfortunately, approaches using these agents may fail due to inadequate formulation of the pesticides. In particular, many formulations are adversely affected by major environmental hindrances. By way of example, rainfall can wash away control agent deposits and sunlight can inactivate the active agent.

Starch and flour have been studied extensively (McGuire and Shasha, 1990; U.S. patent application Ser. Nos. 07/730,763 and 07/913,565, the disclosures of which are incorporated herein by reference) as materials to encapsulate pesticides. Most of this work has been done with granular matrices in efforts to reduce the amount of chemical pesticide needed to control pests or to protect environmentally sensitive pesticides (usually biological control agents) and thus extend their activity. While efforts with these granular formulations have been successful, by far, the majority of pesticides are applied as sprayable formulations. Shasha and McGuire disclose such a sprayable formulation for microbial insecticides consisting of a mixture of cornstarch or flour and sucrose. This formulation enhances and extends the performance of the active agents (U.S. Pat. No. 5,061,697). Formulations of this type are essential for the widespread use of biological control agents and for enabling the reduction of potentially environmentally hazardous chemical pesticides. Formulations that are effective with lower active ingredient rates are possible through the judicious use of protectants, attractants, or other additives that synergize ingredient activity.

However, these formulations require additives at solids rates of 2 to 6% of the spray volume. These formulations, therefore are most useful under low spray volume conditions.

The present invention utilizes a product other than starch to produce a film upon spraying and is distinct from previous technology. While other products from farm commodities have been used as carriers in granular formulations, little work has yet been done with these products for sprayable formulations. For example, wheat gluten has extensively been used in the baking industry but has never before been tested as a pesticide formulation ingredient. Our tests with gluten-based formulations suggest a significant improvement over existing technology because solids rates of a maximum of 1% show improved rainfastness and survival of the active agent. These types of solids rates should extend the usefulness of the formulation to a wider range of spray systems.

BRIEF SUMMARY OF THE INVENTION

The present invention provides, in one aspect, a process of preparing a sprayable gluten-based formulation incorporating a pest control agent comprising admixing an effective amount of a gluten, a pesticidally effective amount of the pest control agent, and water.

The formulation has a non-neutral pH value. In a preferred embodiment, the pH value of the formulation is less than about 5.5 or greater than about 9.5. More preferably, the formulation has a pH value of from about 3.0 to about 5.0 or from about 10.0 to about 12.0.

In a preferred embodiment, the formulation, including the pest control agent, adheres to a plant surface and, more preferably to a plant foliar surface. In another preferred embodiment, the formulation adheres to an external surface of an animal and, preferably skin, fur or hair.

In another aspect, the present invention contemplates a process of decreasing the population of a pest of a living organism comprising delivering to an external surface of the living organism a sprayable gluten-based formulation that (a) incorporates a pest control agent and (b) adheres to that surface. Where the living organism is a plant, the external surface is preferably a foliar surface. Where the living organism is an animal, the external surface is preferably skin, hair or fur. A formulation used in that process is preferably prepared in accordance with a process of the present invention.

The present invention, thus, contemplates a process of decreasing the population of a pest of a living organism comprising the steps of:

(a) formulating the pest control agent into a sprayable gluten-based formulation by admixing a pesticidally effective amount of the pest control agent, an effective formulating amount of gluten and water; and (b) delivering the formulation to the external surface of the living organism.

The gluten and pest control agent used in a process of decreasing the population of a pest of a living organism are the same as set forth above.

In yet another aspect, the present invention contemplates a sprayable gluten-based formulation that incorporates a pest control agent. Preferably, the formulation is made by a process of the present invention.

The present invention provides, in another aspect, a process of decreasing radiation inactivation of a pest control agent. The process comprises adding a pest control agent with a sprayable gluten-based formulation.

The methods and compositions of the present invention solve a significant number of the problems in the previous methods of pest control. A formulation of the present invention adheres to an external surface of a living organism despite exposure of those organisms to environmental forces which dislodge other types of formulations or granules.

DETAILED DESCRIPTION OF THE INVENTION

The present invention provides a process of formulating a chemical or biological material and, in particular a pest control agent, in a sprayable gluten-based formulation and to the composition of such a formulation. The present invention also provides a process of decreasing the population of a pest of a living organism. A formulation of the present invention comprises gluten, a biological or chemical substance such as a pest control agent and an aqueous solvent.

This invention relates to sprayable formulations of chemical and microbial pesticides that are effective in low amounts and resist wash-off from rainfall. Solubilized gluten, specifically wheat gluten, is used to disperse the pesticide and entrap it on leaf or other surfaces. The pesticide then remains viable under harsh environmental conditions. Gluten and specifically wheat gluten compositions are disclosed for the delivery of biological or chemical pest control agents. Due to the low solubility of wheat gluten in water at a neutral pH, a pH adjuster such as citric acid or acetic acid is included to obtain an acidic pH. Alternatively, an alkali component such as ammonium hydroxide, trisodium phosphate or potassium hydroxide is added to obtain an alkaline pH. The pH adjuster can be either dissolved in water prior to the addition of gluten-active ingredient or can be included with the gluten-active ingredient.

I. Process of Preparing a Sprayable Formulation

In one aspect, the present invention provides a process of formulating a pest control agent in a sprayable gluten-based aqueous formulation. Such a formulation process comprises admixing an effective formulating amount of a gluten, a pesticidally effective amount of the pest control agent and an aqueous solvent having a non-neutral pH that allows for solubilization of the gluten.

Where applied to a living organism, the formulation, including the pest control agent, adheres to an external surface of that organism. As used herein, the term "adhere" or any of its grammatical equivalents means that the formulation sticks to a target surface on which the formulation is applied. Exemplary surfaces to which a formulation of the present invention adheres include an external surface of a living organism and artificial surfaces such as those made of glass, metal, plastic, wood, and the like. In a preferred embodiment, a formulation of the present invention adheres to an external surface of a living organism such as a plant or animal. Where the living organism is a plant, a preferred external surface is a foliar surface. Where the living organism is an animal, a preferred external surface is skin, fur or hair.

As used herein, the term "gluten" refers to a water insoluble protein found in cereal grains. Gluten is primarily comprised of gliadin, glutenin, globulin and albumin. Wheat gluten is insoluble in aqueous solutions at neutral pH, but readily soluble in non-neutral aqueous solutions. Wheat gluten comprises about 80–90% of the proteins found in wheat (Krull et at., 1971).

Gluten can be obtained commercially or can be prepared from cereal grains such as wheat. By way of example, wheat gluten can be prepared by mixing wheat flour with an appropriate amount of water to form a dough and then washing out the starch from that dough in a stream of water. Gluten can be commercially prepared in accordance with such a process using either 1) a "dough" or "Martin" process, or 2) "slurry" or "Raisio" process. Gluten, prepared in accordance with any one of the above processes is obtained in a wet form. Dry or "vital" gluten can be obtained from wet gluten by drying.

Gluten has a variety of uses in the food industry. Exemplary such uses include baking, milling and manufacturing pet foods, breakfast cereals, meat, seafood analogs, pasta, cheese analogs, aqua culture feed and snacks. Because of its adhesive, thermo-setting, and film-forming properties, gluten has recently been used in a variety of non-food uses (Krull et at., 1971). Exemplary such non-food uses include the manufacture of biodegradable surfactants, the manufacture of paper coatings and wallpaper adhesives and the production of pressure-sensitive adhesive tapes (Krull et at., 1971; Magnuson, 1985). The present invention describes for the first time, a use of gluten in the preparation of sprayable formulations for use in pest control.

As used herein, a "pest control agent" indicates a substance that serves to repel a pest from a living organism, decrease or inhibit the growth, development or destructive activity of a pest. A pest can be a plant, an animal or a microorganism. Exemplary pests include insects, spiders, nematodes, fungi, weeds, bacteria and other microorganisms. Thus, a pest control agent can be insecticide, a pesticide, a fungicide, a herbicide, antibiotic, an anti-microbial, a recombinant pest control agent and the like. A pest control agent can also be a mixture of two or more agents.

Exemplary pest control agents are dimilin (N—{[(4-chlorophenyl)amino] carbonyl}-2,6-difluorobenzamide), malathion ([(dimethoxyphosphinothioyl)thio]butanedioic acid diethyl ester), carbaryl (1-naphthalenol methylcarbamate) and diazinon® (0,0-diethyl 0-[6-methyl-2-(1-methylethyl)- 4-pyrimidinyl]phosphorothioate); 2,4-D (2,4-dichlorophenoxyacetate sodium salt), a 2,4-D ester (2,4-dichlorophenoxyacetate isopropyl ester); metolachlor (2-Chloro-N-(2-ethyl-6-methylphenyl)-N-(2-methoxy-1-benzenedicarboxylate)); glyphosate(N-(phosphonomethyl)glycine); paraquat (1,1'-dimethyl-4,4'-bipyridinium salt); and trifluralin (1,1,1-trifluoro-2, b-dinitro-N, N-dipropyl-p-toluidine). Pesticides, insecticides, herbicides, fungicides, antimicrobials and antibiotics are commercially available. An exemplary list of such substances can be found in U.S. Pat. No. 4,911,952, the disclosure of which is incorporated herein by reference.

Alternatively, a preferred pest control agent is a recombinant pest control agent. As used herein, a recombinant pest control agent is a pest control agent produced by the use of well known recombinant DNA technology (Sambrook. J., Fritsch, E. F., and Maniatis, T., *Molecular Cloning: A Laboratory Manual,* Cold Spring Harbor Laboratory Press, New York, 1989).

Briefly, when a pest control agent is prepared by recombinant DNA techniques, the recombinant pest control agent is obtained from recombinant host cells which express the recombinant pest control agent. To achieve this, a specific oligonucleotide based upon the sequence of the desired pest control agent is prepared. The oligonucleotide is then inserted into an expression vector, such as any one of the many expression vectors currently available commercially. A host cell is then transformed with the vector, where it will direct the expression of the recombinant version of the pest control agent, which may then be purified from the recombinant host cell. Alternatively, the recombinant pest control agent is a substantially intact recombinant host cell. The preparation of oligonucleotide, vector and transformation of the host cell are within the skill of the ordinary artisan. Exemplary recombinant pest control agents are described in U.S. Pat. Nos. 5,169,629 and 5,352,661, herein incorporated by reference.

A pest control agent can be a biological or chemical material. As used herein, the phrase "biological material" means a living organism or a substance isolated, produced or otherwise derived from a living organism (e.g., a toxin or a hormone). Thus, a biological pest control agent can be an inanimate form of a once living organism. The use of such a biological pest control agent is exemplified hereinafter in Examples 1–3 and 6–9. U.S. Pat. Nos. 5,169,629 ('629) and 5,352,661 ('661) describe the preparation of a recombinant *Bacillus thuringiensis (B.t.)* toxin.

U.S. Pat. Nos. '629 and '661 disclose that recombinant *B.t.* toxin can be produced in a host cell. After the host cell produces a desired concentration of *B.t.* toxin, the host cell can be treated under conditions that prolong the activity of the toxin produced in the cell. When the host cells are treated under such conditions, the host cells remain substantially intact. Alternatively, '629 and '661 disclose that host cell can be applied to the environment in a living state. The use of a recombinant pest control agent, either treated or in a living state, in a sprayable gluten-based formulation provides for improved protection of the pest control agent from environmental conditions. In particular, a pest control agent is protected from being washed away by water and protected from ultraviolet degradation or inactivation by the sprayable gluten-based formulation. The minimization of ultraviolet damage to a commercially available recombinant *B.t.* product is further disclosed in example 16 below.

Exemplary biological pest control agents include bacteria such as *B. thuringiensis,* Baculoviridae, e.g., *Autographa californica* nuclear polyhedrosis virus, protozoa such as Nosema spp., fungi such as Beauveria spp., and nematodes.

As used herein, the phrase "chemical material" means a synthetically prepared compound or composition. Exemplary chemical pest control agents include thiocarbonates, dinitroanilines, organophosphates, and alachlor.

As used herein, the phrase "effective amount" means that amount of a pest control agent sufficient to bring about the desired response (e.g., repel or kill a pest). "A pesticidally effective amount" is that amount which, when delivered to an external surface of a living organism, results in a significant mortality rate of a pest when compared to the mortality rate of that same pest exposed to a living organism not treated with that agent.

A pest control agent can further comprise an additive or adjunct such as a dispersant, a phagostimulant (a feeding stimulant), an attractant, an ultraviolet light protectant, a preservative and an inert filler. Examples of such additives can be found in U.S. Pat. No. 4,911,952, the disclosure of which is incorporated herein by reference.

In a preferred embodiment, the additive is an attractant or a phagostimulant. An attractant is preferably an aqueous, non-soluble, or hydrophobic substance that attracts a pest to the spray deposit. A phagostimulant is a substance that stimulates ingestion of the spray deposit.

A preferred attractant is a pheromone or a volatile feeding attractant such as p-methoxycinnamaldehyde. An exemplary and preferred phagostimulant is cucurbitacin obtained from the powdered, dried root of the buffalo gourd, or Coax®, a feeding stimulant containing cotton seed flour, sugar, vegetable lipid oil and ethoxylated ester (CCT Corporation, Litchfield Park, Ariz.). Exemplary sugars are mono-, oligo- and polysaccharides containing from about 1 to about 50 saccharide units. In a preferred embodiment, a sugar is a disaccharide such as sucrose, molasses or corn syrup solids.

Exemplary formulations comprising one or more of the above ingredients are described in detail hereinafter in Examples 1 through 17.

Admixing is carried out at a temperature of from about 5° C. to about 100° C. and, preferably, at a temperature of from about 10° C. to about 25° C. The gluten, pest control agent, and water can be admixed in any order.

Typically, the concentration of gluten in a formulation of the present invention is from about 0.1 percent by weight (grams/100 ml) to about 5 percent by weight. More preferably, the concentration of gluten is from 0.25 percent by weight to about 1.5 percent by weight. The only limitation on the concentration of gluten is the solubility of gluten. Solubility is enhanced at non-neutral pH values.

The pH value of a formulation of the present invention is adjusted with an alkalinizing or an acidifying agent. Any alkalinizing or acidifying agent can be used to adjust formulation pH so long as that agent does not adversely affect the formulation or the biological or chemical substance contained therein. In a preferred embodiment, an acidifying agent is an organic acid. A preferred organic acid is citric acid. The amount of an acidifying agent used depends, as is well known in the art, upon the strength of that acidifying agent and the desired pH.

The formulation has a non-neutral pH value. In a preferred embodiment, the pH value of the formulation is less than about 5.5 or greater than about 9.5. More preferably, the formulation has a pH value of from about 3.0 to about 5.0 or from about 10.0 to about 12.0.

A preferred alkalinizing agent is a basic salt. More preferably, an alkalinizing agent is a metal hydroxide such as NaOH or KOH. The amount of an alkalinizing agent used depends, as is well known in the art, upon the dissociation constant of that agent and the desired pH.

A formulation of the present invention can also comprise a buffer to maintain the pH at a predetermined value. Any buffer can be used so long as that buffer does not adversely affect the formulation or the pest control agent contained therein. A buffer can also be used as the acidifying or alkalinizing agent. Thus, in one embodiment, formulation pH can be set and maintained with a form of buffer pairs such as phosphoric acid-phosphate, citric acid-citrate and acetic acid-acetate.

A formulation of the present invention can also be prepared to comprise water-dispersible granules. In accordance with such an embodiment, a formulation comprises, in addition to a pest control agent, 1) an agglomerating agent that promotes formation of granules that contain gluten, 2) a dispersing agent that promotes separation of gluten particles upon contact with the aqueous solvent, or 3) both an agglomerating and a dispersing agent. In a preferred embodiment, a dispersing or agglomerating agent is premixed with gluten prior to the addition of the aqueous solvent. A preferred dispensing agent or an agglomerating agent is a vegetable oil such as corn oil or soybean oil. A preferred agglomerating agent is molasses. A description of a formulation made by precoating gluten with corn oil can be found hereinafter in Example 3.

II. Process of Pest Control

In another aspect, the present invention contemplates a process of decreasing the population of a pest of a living organism, which process comprises the steps of:

(a) formulating a pest control agent into a sprayable gluten-based aqueous formulation in accordance with a process of the present invention; and (b) delivering a pesticidally effective amount of the formulation to an external surface of the organism.

A pest control agent that can be used with this process is the same as set forth above in relation to a process of preparing a sprayable formulation. The selection of a pest control agent depends upon the pest to be controlled as well as the nature of the living organism to be protected.

Preferably, the pest control agent comprises at least one of *Bacillus thuringiensis,* entomopoxvirus, a chemical insecticide, and a pest attractant. In a more preferred embodiment, a pest control agent comprises a pesticide and an attractant, the purpose of which is to lure a pest to the formulation containing the pest control agent. The attractant can be volatile such as a pheromone.

A pesticidally effective amount of a pest control agent in a formulation is delivered to a living organism. Means for determining a pesticidally effective amount for a given pest control agent are well known in the art. In a preferred embodiment, a formulation is sprayed onto an external surface of the living organism. By way of example, formulations are applied to greenhouse grown plants using a DeVries Research Track Sprayer Booth. The spray is calibrated to deliver formulation at a rate equalling 25 gal/A at 59 PSI with a single 8002 flat fan nozzle.

Use of a formulation of the present invention has the advantage of decreasing the amount of pest control agent needed to protect a given area of surface area by minimizing loss of delivered pest control agents due to environmental conditions. Environmental disturbances include wind, rain and snow. A major problem in the use of pest control agents is the loss of such agents from target organisms. In the present invention, a formulation is produced which, upon spraying on a surface, permits agents in that formulation to adhere to that surface even in the presence of additional water. The use of a formulation of the present invention thus allows for earlier application of a pest control agent and extends the "window" of application necessary for the economic control of a pest that can enter an area over an extended period of time. Still further, a process of the present invention increases the effectiveness of a pest control agent. Because a control agent adheres to surfaces for an extended period of time, the contact between the pest control agent and the target organism to which it is applied is substantially prolonged.

III. Sprayable Gluten-Based Formulation

In a still further aspect, the present invention contemplates a sprayable gluten-based formulation that incorporates a biological or chemical substance and, preferably a pest control agent. As used herein, the term "gluten-based" indicates that a formulation of the present invention comprises gluten.

A sprayable-gluten based formulation of the present invention comprises an effective formulating amount of gluten, a pesticidally effective amount of a pest control agent and an aqueous solvent. Typically, the concentration of gluten in a formulation of the present invention is from about 0.1 grams/100 ml to about 5 grams/100 ml. Even more preferably, the concentration of gluten is from about 0.25 grams/100 ml to about 1.5 grams/100 ml. A gluten-based formulation of the present invention has a non-neutral pH value and preferably has a pH value of from about 3.0 to about 5.0 or from about 10.0 to about 12.0. A preferred solvent is water. As set forth above, a formulation of the present invention can further comprise acidifying or alkalinizing agents, a buffer and an additive such as a pest attractant or a phagostimulant. A formulation of the present invention is preferably made by a process as set forth above.

Upon application of a formulation of the present invention to a surface, a pest control agent in the formulation adheres to a variety of surfaces including but not limited to glass, metal, plastic, wood, plastic and to an external surface of a living organism such as an animal or plant. In a preferred embodiment, an external surface is an external surface of a plant or animal. Exemplary and preferred surfaces are a plant foliar surface, animal skin, fur and hair. In a preferred embodiment, a formulation of the present invention is made by a process of this invention.

In another aspect, the present invention provides a process for decreasing radiation degradation or inactivation of a pest control agent. The process comprises admixing at a temperature of from about 5° C. to about 100° C. a pest control agent with a protective amount of a gluten and an aqueous solvent to form a sprayable gluten-based formulation. The formulation further comprises molasses, vegetable oil, $CaCl_2$, an alkalinizing agent, or an acidifying agent. Degradation or inactivation of pest control agents by radiation, in particular by ultraviolet radiation, is decreased or minimized by a sprayable gluten-based formulation as provided herein.

As used herein, the term "radiation" refers to energy in the form of electromagnetic waves that a pest control agent is exposed to during use and after application. For the purposes of the present invention, radiation that a pest control agent is exposed to during use is ultraviolet, visible and infrared radiation.

Preferably, the protective amount of gluten is from about 0.1 grams to about 5 grams per 100 ml of the sprayable gluten-based formulation. Alternatively, the protective amount of gluten is from about 0.25 grams to about 1.5 grams per 100 ml of the sprayable gluten-based formulation.

Example 17 below discloses the ultraviolet protective effects of a sprayable gluten-based formulation as disclosed herein. The results of a laboratory test and the results of a field test are disclosed in Example 17. In the field study, cabbage plants were sprayed with *B.t.* prepared with and without a sprayable gluten-based formulation. After 1, 2, 4 and 7 days, leaf tissues were removed and fed to neonate *Trichoplusia ni* and mortality was determined. After 7 days of solar exposure, the *B.t.*/water formulation retained only 22% of the original *B.t.* activity. In marked contrast, the *B.t.*/gluten-based formulation retained about 75% of the original activity, an increase of roughly 300%.

The following examples have been included to illustrate preferred modes of the invention. Certain aspects of the following examples are described in terms of techniques and procedures found or contemplated by the present inventors to work well in the practice of the invention. These examples are exemplified through the use of standard laboratory practices. In light of the present disclosure and the general level of skill in the art, those of skill will appreciate that the following examples are intended to be exemplary only and that numerous changes, modifications and alterations can be employed without departing from the spirit and scope of the invention.

EXAMPLES

All new formulations containing technical grade *B. thuringiensis* (*Bt*), supplied by Abbott Laboratories as a bioassayed preparation containing 70,000 International Units/mg were compared against a commercial formulation of *Bt*, (Dipel 2X), containing 32,000 international units (Iu)/mg. Tests were conducted either under dry and/or wet conditions. Under wet conditions, after application of formulations, each treatment received 2 inches of simulated rain in a spray chamber. For bioassays, unless otherwise stated, cotton was used as the test plant and European corn borer larvae were used as the test insect.

GENERAL TESTING PROCEDURE

A. Application of formulations. Formulations were applied to whole cotton plants using a DeVries Research Track Sprayer Booth. The sprayer is calibrated to deliver formulation at a rate equalling 25 gal/A at 59 PSI with a single 8002 flat fan nozzle.

B. Simulated rainfall. After allowing the plants to dry, half were subjected to simulated rainfall in the sprayer booth. Approximately 2 inches (as measured by a rain gauge) rain was allowed to fall over a 1.45 hr period through a FL5VC Full cone nozzle at 32 PSI. Continuous movement of the nozzle, back and forth, allowed for an even dispersion of water throughout the chamber and over the leaves.

C. After the plants dried, leaf disks (33 $cm^2$) were cut from the treated plants and inverted in a 9 cm diameter plastic petri dish lined with white filter paper. Ten European corn borer neonate larvae (*Ostrinia nubilalis*) (ECB) were added to each dish and then each dish was twice wrapped with parafilm to seal the edges. After 3 days in the dark at 27° C., dishes were opened and percent mortality obtained. In general, 10 leaf disks were tested for each treatment.

EXAMPLE 1

500 milliliters (ml) of a 0.011% (w/v) solution of sodium hydroxide and 0.15% (w/v) urea in deionized water were mixed in a blender with *B. thuringiensis* tech powder (50 mg). Formulations were made without gluten or with either 5 grams (1%) or 2.5 grams (0.5%) of gluten. The pH of the formulations was about 10.6.

| FORMULATION | % ECB MORTALITY | |
|---|---|---|
| | RAIN | NO RAIN |
| Untreated control | | 0 |
| Gluten 1% - NaOH-urea control | | 12 |
| NaOH-urea-Bt tech | 15 | 75 |
| Gluten 0.5% - NaOH-urea-Bt tech | 24 | 94 |
| Gluten 1% - NaOH-urea-Bt tech | 71 | 94 |
| Dipel 2x | 8 | 87 |

EXAMPLE 2

The following gluten formulations were made:

A. Dipel 2× (88 mg) was dispersed in 200 ml of a 0.1% (w/v) molasses solution in deionized water.

B. *B. thuringiensis* technical powder (40 mg) was dry mixed with gluten (2 g) and mixed in a Waring blender with 200 ml of an aqueous solution comprising deionized water, 0.1% (w/v) molasses and 0.1% (w/v) citric acid to yield a formulation with a pH of about 3.5.

C. *B. thuringiensis* technical powder (40 mg) was dry mixed with gluten (2 g) and mixed in a Waring blender with 200 ml of an aqueous solution comprising deionized water, 0.1% (w/v) molasses and 0.05% (w/v) KOH.

D. *B. thuringiensis* technical powder (40 mg) was dry mixed with gluten which was precoated with corn oil in a ratio of 10:1 (w/w) and mixed in a Waring blender with 200 ml of an aqueous solution comprising deionized water, 0.1% (w/v) molasses and 0.1% (w/v) citric acid to yield a formulation with a pH of about 3.5.

E. *B. thuringiensis* technical powder (40 mg) was dry mixed with gluten which was precoated with corn oil in a ratio of 10:1 (w/w) and mixed in a Waring blender with 200 ml of an aqueous solution comprising deionized water, 0.1% (w/v) molasses and 0.05% (w/v) KOH.

F. Calcium chloride dihydrate (2 g) was dissolved in molasses (20 g) to form a molasses solution. Gluten (10 g) was dispersed with that molasses solution (2 g) to form dispersible granules. A sample of the gluten-molasses dispersible granules (2 g) was mixed with 200 ml of a 0.1% (w/v) citric acid solution and 40 mg. *Bt* tech as in (B).

The results of studies using the above formulations are summarized below.

| FORMULATION | % ECB MORTALITY | |
|---|---|---|
| | RAIN | NO RAIN |
| Untreated control | — | 3.9 |
| A | 28.1 | — |
| B | 57.1 | 92.6 |
| C | 81 | 98.6 |
| D | 66 | 68.2 |
| E | 75.5 | 98.8 |
| F | 62.7 | 92.6 |

EXAMPLE 3

The following formulations were prepared.

A. Molasses control, 0.2% (w/v) molasses in deionized water.

B. Dipel 2× control, 22 mg active ingredient in deionized water (50 ml).

C. Dipel 2×, (22 mg) in 0.2% (w/v) molasses in deionized water (50 ml).

D. *Bt* tech (10 mg) was added to a 0.1% (w/v) citric acid—deionized water solution (50 ml). 0.5 g gluten was added to the solution.

E. *Bt* tech (10 mg) was added to a 0.1% (w/v) citric acid—0.2% (w/v) molasses—deionized water (50 ml) solution. 0.5 g gluten was added to the solution.

F. *Bt* tech (10 mg) was added to a 0.025% (w/v) KOH—deionized water (50 ml) solution. 0.5 g gluten was added to the solution.

G. *Bt* tech (10 mg) was added to 0.025% (w/v) KOH—0.2% (w/v) molasses—deionized water solution. 0.5 g gluten was added to the solution.

The results from studies using the above formulations are summarized below.

| FORMULATION | % ECB MORTALITY | |
|---|---|---|
| | RAIN | NO RAIN |
| Untreated control | — | 14.5 |
| A | — | 8 |
| B | 28.4 | 89.2 |
| C | 32.3 | 99 |
| D | 61 | 59.4 |
| E | 73.2 | 96.2 |
| F | 77.2 | 98.2 |
| G | 62.2 | 100 |

EXAMPLE 4

Gluten and acid can be added together or separately. Wheat gluten (20 g) was dry mixed with powdered citric acid hydrate (2 g) and then added to deionized water (2 liters) in a blender. This yielded a mixture of solubilized gluten containing 1.1% (w/v) solid with a pH of 3.54.

EXAMPLE 5

Gluten and alkali can also be added together before addition to water. Wheat gluten (20 g) was dry mixed with powdered potassium hydroxide (2 g) and then added to deionized water (2 liters) in a blender. This yielded a mixture of solubilized gluten containing 1.1% (w/v) solid with a pH of 11.78. When the experiment was repeated using tap water instead of deionized water, the pH was 11.17.

Wheat gluten (60 g) was dry mixed with powdered potassium hydroxide (3 g) and then added to deionized water (2 liters) in a blender. This yielded a mixture of solubilized gluten with a pH of 11.78, Which after dilution with deionized water (4 liters) had a pH of 11.35.

EXAMPLE 6

The performance of *Bt* tech versus Dipel 2X in the presence or absence of gluten was compared. The dose of Bt tech used was 10 mg/50 ml deionized water or the equivalent amount of Dipel 2X (22 mg/50 ml deionized water). The gluten concentration was 1% and the concentration of $Na_3PO_4$ (TSP) was 0.1% (w/v).

The results from studies using the above formulations are summarized below.

| | % ECB MORTALITY | |
|---|---|---|
| FORMULATION | RAIN | NO RAIN |
| Untreated control | — | 12.8 |
| Gluten TSP + Dipel 2X | 46.5 | 100 |
| Gluten TSP + Bt tech | 87.2 | 97.2 |
| Dipel 2X + TSP | 19.0 | 95 |
| Tech Bt + TSP | 13 | 99 |
| Dipel 2X | 15.5 | 97 |
| Bt tech | 13.7 | 94.5 |

EXAMPLE 7

The efficacy of *Bt* tech treatment was compared with 20 mg Dipel 2X/50 ml deionized water, using several gluten concentrations and in the presence of $Na_3PO_4$ (TSP). The $Na_3PO_4$ concentration was 0.05% (w/v) and had a pH of 9.4.

The results from studies using the above formulations are summarized below.

| | % ECB MORTALITY | |
|---|---|---|
| FORMULATION | RAIN | NO RAIN |
| Dipel 2X in Water | 8 | 78 |
| Dipel 2X + TSP | 44 | 85 |
| Gluten 0.25% + TSP + Dipel 2X | 41 | 80 |
| Gluten 0.50% + TSP + Dipel 2X | 54 | 87 |
| Gluten 1.0% + TSP + Dipel 2X | 65 | 80 |

EXAMPLE 8

Deionized water (180 ml) was mixed in a blender with an ammonium hydroxide solution (5 ml) to yield a solution of pH 11.0. Wheat gluten (20 g) and 40 mg *Bt* tech powder (70,000 I.U./mg) were added and the formulation was sprayed on cabbage leaves to control cabbage looper (*Trichoplusia ni* [*T. ni*]). Results were compared against *Bt* tech in the absence of gluten and against Dipel 2X. Larval mortality after 6 days exposure on cabbage plants is summarized below.

| FORMULATION | % T. NI MORTALITY |
|---|---|
| Control - Water | 18 |
| Control - Bt tech | 43 |
| Control Dipel 2X | 65 |
| Gluten Bt tech | 84 |

EXAMPLE 9

The efficacy of *Bt* in a gluten formulation was tested in field trials against *Trichoplusia ni* (Hubner). Formulations were applied to cabbage leaves under rain and no rain conditions. The leaves were examined after 0, 2, 4 and 7 days and results are expressed in percentage mortality of *Trichoplusia ni.* Rain was simulated using evenly spaced Rainbird brand impact-style lawn sprinklers. Water was delivered at approximately 0.5 inches per hour over the canopy. Approximately 2 inches rain was applied. Plants not receiving rain were covered with plastic tents. The formulations tested were:

A) Water only

B) 0.1% (w/v) molasses control

C) Dipel 2X (4 g/L)

D) Dipel 2X (4 g/L) in 0.1% (w/v) molasses

E) *Bt* tech (1.83 g/L)+gluten (1%) (w/v)+citric acid (CA) (0.1%) (w/v)

F) *Bt* tech (1.83 g/L)+gluten (1%) (w/v)+citric acid (CA) (0.1%) (w/v)+mol (0.1%) (w/v)

G) *Bt* tech (1.83 g/L)+gluten (1%) (w/v)+KOH (0.025%) (w/v) H) *Bt* tech (1.83g/L)+gluten (1%)(w/v)+KOH (0.025%) (w/v)+mol (0.1%) (w/v)

The results from studies using the above formulations are summarized below.

| | DAYS AFTER TREATMENT | | | | | | | |
|---|---|---|---|---|---|---|---|---|
| Formulation | 0 No Rain | 0 Rain | 2 No Rain | 2 Rain | 4 No Rain | 4 Rain | 7 No Rain | 7 Rain |
| A | 23.8 | 14.7 | 14.9 | 7.4 | 17.8 | 14.8 | 11.2 | 44.4 |
| B | 12.3 | 13.0 | 6.3 | 6.6 | 13.1 | 13.5 | 15.6 | 16.6 |
| C | 100.0 | 85.3 | 100.0 | 37.2 | 77.4 | 19.5 | 19.2 | 28.8 |
| D | 100.0 | 96.3 | 88.1 | 57.4 | 43.7 | 16.2 | 30.5 | 5.9 |
| E | 94.4 | 86.6 | 64.6 | 90.8 | 69.4 | 92.0 | 18.6 | 50.4 |
| F | 100.0 | 99.0 | 82.9 | 89.8 | 79.2 | 93.8 | 30.1 | 32.5 |
| G | 100.0 | 95.3 | 100.0 | 98.2 | 96.7 | 93.6 | 42.5 | 27.4 |
| H | 100.0 | 100.0 | 99.2 | 95.6 | 95.7 | 89.7 | 39.8 | 36.3 |

EXAMPLE 10

Molasses (20 g) was mixed thoroughly with corn oil (1 g). To obtain water dispersible gluten particles, gluten (20 g) was mixed with a molasses-oil mixture (5 g) and allowed to dry at room temperature. The resulting products were granules that dispersed in water quickly and could be applied by spraying.

About 50 ml of dispersible gluten was added to tap water (1 g), followed by the addition of wettable powdered elemental sulfur (1 g). The pH of the mixture was adjusted to 11 by the addition of a diluted KOH solution. Freshly harvested cotton leaves (9 cm in diameter) were treated with the gluten-sulfur mixture (0.7 ml). As a control, the experiment was repeated using cotton leaves treated with a suspension of elemental sulfur as above but without gluten. Both samples were first allowed to dry at room temperature, followed by rinsing with tap water (1 liter) applied over a 60 seconds period. The leaves were then dried at 75° for 1 hour and analyzed for sulfur.

Sulfur in control sample=0.9%

Sulfur in gluten sample=1.9% (corrected for S present in gluten).

The experiment was repeated using corn leaves with the following results:

Sulfur in control sample=1.2%

Sulfur in gluten sample=2.8% (corrected for S present in gluten).

In another experiment, water dispersible gluten (1 g) was mixed with tap water (100 ml) along with Weedone=2, 4-D formulation (1 g). The pH was adjusted to 11 as above to yield a stable emulsion of the herbicide to control broad-leaf weeds.

EXAMPLE 11

The following gluten formulations were made with the herbicide trifluralin.

(A) Gluten (12.5 g) was mixed in a blender with a 0.2% (w/v) KOH solution (250 ml). A sample of this mixture (19 g) was blended with trifluralin emulsifiable concentrate (1 g) containing 44% active ingredient (w/v).

(B) Experiment (A) was repeated, substituting the alkali solution with 0.2% citric acid.

(C) Trifluralin emulsifiable concentrate (1 g) was mixed with water (19 ml).

Samples of (A), (B) and (C) were placed as droplets onto separate glass microscope slides. Following drying at ambient temperature, the slides were rinsed with n-hexane. Trifluralin from (A) and (B) remained practically intact, but the active ingredient from (C) was completely washed out. This test revealed that the film formed with the gluten, under acidic or alkaline pH conditions, effectively encapsulated the trifluralin.

In another experiment, slides (A), (B) and (C) were dried at ambient temperature, then subjected to enhanced evaporation of the active ingredient at 60° C. for 2 hours. The trifluralin remained essentially intact in (A) and (B) but it essentially all evaporated from (C). Furthermore, the gluten film in (A) and (B) adhered to the glass and resisted wash out with water.

Additional studies were carried out with the following formulations.

(D) Trisodium phosphate (1 g) was dissolved in water (2 ml), mixed thoroughly with gluten (9 g), and dried at ambient temperature to yield a fine powder with a pH of 9.8 (1% conc. in deionized water). Part of this mixture (8 g) was blended with a melt of technical grade trifluralin (2 g) to yield a water dispersible product. 1 g was added to 100 ml water and applied dropwise to glass microscope slides. A film formed upon drying that did not dislodge during the application of 1L water over a 30 second period. Retention of the characteristic yellow color of trifluralin indicated retention of the herbicide.

(E) Trisodium phosphate (TSP) (5 g) was dissolved in water (9 ml) and dextrin 200 (commercial product made by Staley, Decatur, Ill.; 5 g) and mixed with gluten (45 g) using a morter and pestel. Drying at ambient temperature produced a fine powder which passed 40 mesh. A melt of technical grade trifluralin (2 g) was mixed with gluten-TSP-dextrin (8 g) to yield a water dispersable product.

(F) Citric acid monohydrate (0.5 g) was mixed with $CaCl_2.2H_2O$ (0.5 g), gluten (18 g) and a melt of technical grade trifluralin (2 g) to yield a water dispersible product with a pH of 3.75 (1% solid in deionized water).

EXAMPLE 12

Paraquat is a herbicide commonly used to defoliate cotton prior to harvest. Gluten (6 g) was mixed in a blender with a 0.1% (w/v) citric acid solution (600 ml) and an aqueous solution of paraquat (29% active ingredient, 10 ml). Mature cotton was sprayed in the field to run-off with this mixture. Within hours, leaves began to curl and wither and, after 2 days, leaves were brown. Within 4 days, leaves had fallen off.

EXAMPLE 13

*Sitophilus zeamais*

2 grams gluten dissolved in 200 ml 0.05% KOH containing 0.8 g technical diazinon® (trade name). 5 grams solution was mixed with 100 g corn seeds and allowed to dry which is equivalent to 0.2 g active ingredient per 1 kg seeds. Controls consisted of seeds coated with gluten solution only (no diazinon®). Adult maize weevils (*Sitophilus zeamais*) were placed in a 28 ml cup with 5 corn seeds. Mortality was assessed 8 hrs later. All weevils exposed to corn seeds treated with diazinon® died whereas none of the insects on control seeds died.

*Lasioderma serricorne, Carpophilus hemipterus, Oryzaephilus surinamensis*

2 grams gluten was dissolved in 200 ml 0.05% KOH containing 0.2 g technical diazinon®. Controls consisted of gluten solution without diazinon®. Approximately 10 drops of solution was placed in the bottom of a plastic petri dish and allowed to dry overnight. Adult insects were placed in each dish and a wet dental wick was added to each dish to supply moisture. Mortality was assessed 8 hrs later.

| | PERCENT MORTALITY | |
|---|---|---|
| INSECT SPECIES | WITH DIAZINON ® | CONTROL |
| *Lasioderma serricorne* | 100 | 0 |
| *Carpophilus hemipterus* | 100 | 30 |
| *Oryzaephilus* | 45 | 0 |

| PERCENT MORTALITY | | |
|---|---|---|
| INSECT SPECIES | WITH DIAZINON ® | CONTROL |
| surinamensis | | |

EXAMPLE 14

2 grams gluten was added to 100 ml 0.1% KOH containing 2 grams elemental sulfur. As a control, 2 grams sulfur was added to 100 ml 0.1% KOH without gluten. Each sample was spread on 6 glass microscope slides and allowed to dry. Each slide was then placed under a sink faucet and allowed to receive approximately 2 liters water in 50 sec. After drying, slides were visually observed for presence or absence of sulfur.

After washing, no sulphur was visible on slides that received the sample without gluten. However, sulfur was visible after washing on those slides that received the sample containing sulfur plus gluten.

EXAMPLE 15

*Autographa california* nuclear polyhedrosis virus was formulated with gluten using both the acid and base procedures. To prepare the acid formulation, 1 gram gluten was added to 100 ml of 0.1% citric acid (pH 3.3). To prepare the basic formulation, 1 gram gluten was added to 100 ml of 0.1% ammonium hydroxide solution (pH 10.1). Virus polyhedral inclusion bodies (PIBS) were then added to the solutions. As a control, PIBS were also added to water. Concentration of the PIBS was $10^4$ per ml and $10^6$ per ml. 100 ul of a solution was spread evenly over a 33 cm² cotton leaf disk and allowed to dry. Leaf disks were then placed in a plastic petri dish and 5 neonate *Heliothis virescens* larvae were added. The dish was sealed with parafilm and held for three days. Insects were then transferred to individual diet cups and held an additional 10 days. For each formulation, 10 petri dishes were set up. The gluten formulations did not appear to negatively alter the activity of the virus despite the high or low pH, as shown in the table below.

| FORMULATION | PIBS/ML | % MORTALITY |
|---|---|---|
| Water | 0 | 2.5 |
| Water | $10^4$ | 4.4 |
| Water | $10^6$ | 82.9 |
| Acid | 0 | 0 |
| Acid | $10^4$ | 31.8 |
| Acid | $10^6$ | 88.9 |
| Base | 0 | 4.5 |
| Base | $10^4$ | 19.1 |
| Base | $10^6$ | 86.7 |

EXAMPLE 16

A study was conducted to determine the effect of gluten on rainfastness of a Mycogen Company's *Bacillus thuringiensis* product. Gluten (0.5 g) was dissolved in 50 ml 0.05% KOH solution. Technical product (40 mg) called cream by Mycogen personnel was then added to the KOH-Gluten mixture. As controls, 40 mg cream was added to 50 ml water and the commercial product called MVP® was also tested at the rate of 80 mg per 50 ml water. Both Mycogen MVP® and cream provide *B.t.* toxins encapsulated in substantially intact cells. Plants were treated and mined upon as previously described and the European corn borer was used as the test insect.

Rainfastness: It is clear from the data in table below that the Mycogen products readily washed of with 5 cm min. Gluten, however, retained significantly higher residual activity. Results are expressed in terms of average percent mortality of European corn borers per leaf disk (10 larvae per disk; 10 disks per treatment).

| FORMULATION | NO RAIN | 5 CM SIMULATED RAIN | ORIGINAL ACTIVITY REMAINING |
|---|---|---|---|
| Mycogen MVP ® | 100 | 1 | 1% |
| Cream | 97 | 0 | 0% |
| Gluten + Cream | 93 | 48 | 52% |
| Untreated | 2 | — | — |

EXAMPLE 17

Laboratory Studies

Gluten has previously been shown to keep pesticides in the target zone in the presence of rain. Without gluten, the pesticides wash off the plant and are lost. We have recently discovered that gluten also helps protect sensitive pesticides such as *Bacillus thuringiensis* from sunlight. It is well known that sunlight, especially wavelengths in the UV portion of the spectrum, is detrimental to biological pesticides and may cause loss of activity within a few hours.

Gluten formulations (1% w/v) were prepared as previously described in Example 3 and Example 4.

To measure solar stability, 100 µl of formulation was applied to 33 cm² leaf disk which had been marked onto a cotton leaf while still on the plant. For each formulation, 20 disks were treated. Ten disks received solar treatment and the other ten remained in the laboratory under ambient light conditions. The solar treatment consisted of placing the cotton plants under a SunTest CPS light source so that all ten marked leaves were equidistant from the light. Plastic, transparent to the light, was placed between the light and the plants to avoid excessive drying of the leaf tissue. Leaves were exposed for eight hours.

After all formulations were exposed, leaf disks were removed, placed in petri dishes with ten neonate *Ostrinia nubilalis* and incubated for three days. Mortality was then assessed. Results are presented in the table below.

RESULTS OF LABORATORY ASSAYS

|  |  |  |  | PERCENT MORTALITY | | |
| --- | --- | --- | --- | --- | --- | --- |
| DATE | BOOK/PAGE | BT SOURCE | FORMULATION | BEFORE SOLAR | AFTER SOLAR | OAR |
| 11-09-93 | 15151/054 | Abbott | Water only | 80.27 | 31.35 | 39.06 |
|  |  |  | Gluten/KOH | 95.50 | 87.78 | 91.91 |
| 11-22-93 | 15151/057 | Abbott | Water only | 82.78 | 19.03 | 22.99 |
|  |  |  | Gluten/KOH | 93.08 | 73.00 | 78.43 |
|  |  |  | Gluten/Acetic | 76.29 | 36.89 | 48.35 |
| 02-15-94 | 15151/084 | Abbott | Water only | 89.87 | 18.01 | 20.04 |
|  |  |  | Gluten/KOH | 87.87 | 76.02 | 86.51 |
|  |  |  | Gluten/Acetic | 50.58 | 24.93 | 49.28 |
| 04-11-94 | 15237/008 | Abbott | Water only | 85.42 | 34.57 | 40.47 |
|  |  |  | Gluten/KOH | 97.78 | 83.89 | 85.80 |
| 05-10-94 | 15237/033 | Abbott | Water only | 67.94 | 24.33 | 35.82 |
|  |  |  | Gluten/KOH | 93.89 | 71.94 | 76.62 |
| 06-28-94 | 15237/047 | Mycogen | Water only | 93.42 | 78.22 | 83.73 |
|  |  |  | Gluten/KOH | 91.17 | 83.36 | 91.44 |

OAR = Percentage Original Activity Remaining based on a ratio of after solar mortality divided by before solar mortality. This measure is more reflective of actual protection because before exposure mortality may vary with formulation or trial due to insect fitness and the feeding stimulant properties of the gluten formation.

Field Studies

To determine the relative impact of actual sunlight on persistence of insecticidal activity of *Bacillus thuringiensis*, a small plot replicated field test was established. Cabbage was transplanted into small plots at NCAUR. Gluten formulation (1% w/v) was prepared as previously described with KOH. Treatments were applied with a $CO_2$ charged sprayer at the rate of 30 gallons of water per acre, 16 billion International units of *Bacillus thuringiensis* per acre, a pressure of 30 psi, and a ground speed of approximately 4 mph. After treatments were applied and allowed to dry, plastic shields were erected over the tops of the plants to either green out all light (black plastic) or green out only rain (clear plastic). In addition, some plants were left uncovered. At one, two, four and seven days after application, leaf tissue was removed from each formulation by cover treatment and brought into the laboratory. Leaf disks were cut out, placed in plastic petri dishes lined with filter paper, and ten neonate *Trichoplusia ni* (cabbage looper) were added. After three days, percentage mortality was assessed. Results are presented in the table below.

RESULTS OF FIELD TEST

|  |  | PERCENTAGE MORTALITY DAYS AFTER APPLICATION | | | | |
| --- | --- | --- | --- | --- | --- | --- |
| FORMULATION | COVER | 1 | 2 | 4 | 7 | OAR |
| Trial 1. | None | 93.54 | 77.93 | 65.92 | 35.43 | 37.87 |
| Water Only | Clear | 94.74 | 86.57 | 62.12 | 21.16 | 22.33 |
|  | Black | 95.14 | 97.75 | 68.86 | 87.40 | 91.86 |
| Gluten | None | 96.78 | 91.27 | 86.20 | 89.20 | 92.17 |
|  | Clear | 95.78 | 99.09 | 87.23 | 71.67 | 74.82 |
|  | Black | 97.78 | 100.00 | 96.18 | 94.55 | 96.70 |
| Untreated | None | 42.60 | 38.15 | 35.75 | 4.55 |  |
|  | Clear | 50.50 | 52.89 | 42.13 | 21.09 |  |
|  | Black | 37.82 | 60.24 | 7.89 | 21.75 |  |
| Trial 2 | None | 92.06 | 80.34 | 40.70 | 14.36 | 15.60 |
| Water Only | Clear | 98.00 | 99.00 | 61.87 | 19.22 | 19.61 |
|  | Black | 100.00 | 100.00 | 93.84 | 74.28 | 74.28 |
| Gluten | None | 97.18 | 97.09 | 72.23 | 63.97 | 65.82 |
|  | Clear | 96.00 | 99.00 | 71.46 | 51.69 | 53.84 |
|  | Black | 100.00 | 94.18 | 97.18 | 81.17 | 81.17 |
| Untreated | None | 45.08 | 12.77 | 3.74 | 13.91 |  |
|  | Clear | 15.44 | 51.91 | 15.22 | 9.16 |  |
|  | Black | 18.91 | 10.72 | 3.25 | 5.55 |  |

OAR = Percentage Original Activity Remaining was determined by dividing day 7 mortality by day 1 mortality.

The foregoing examples demonstrate the effectiveness of a formulation of the present invention. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below and all references cited herein are incorporated herein by reference to the extent that they supplement, explain, provide a background for, or teach methodology, techniques, and/or compositions employed herein.

Adamek et al., U.S. Pat. No. 3,111,416, (1963).
Arannnyi et al., U.S. Pat. No. 3,607,370 (1971).
Blish, M. J., *Advances in Protein Chemistry*, II:337–359 (1945).
Chung, O. K., *Cereal Foods World*, 31:242–256 (1986).
Dunkle, R. L., and Shasha, B. S., *Environ. Entomol.* 17:120–126 (1988).
Hughes, P. R., and Wood, H. A., *J. Invertebr. Pathol.* 37:154–159 (1981).
Koestler, R. C., Microencapsulation by interfacial polymerization techniques—agricultural applications, pp. 117–132. *In* A. F. Kydonieus [ed.] Controlled release technologies: methods, theory, and applications. CRC Press, Boca Raton (1981).
Krull, L. H. and Inglett, G. E., *Cereal Science Today*, 16:232–236 (1971).
Krull, L. H. and Wall, J. S., *Canadian J. of Biochem.*, 47:581–585 (1969).
Lampman, R. L. and Metcalf, R. L., *Environ. Entomol.* 17:644–648 (1988).
Lance, D. R., *J. Chem. Ecol.* 14:1177–1185 (1988).
Lance, D. R., and Sutter, G. R., *J. Econ. Entomol.* 83:1085–1090 (1990).
Lund, R. L., MSUSTAT Statistical Analysis Package, vers 4.1. Research and Development Institute. Bozeman, MT (1988).
Magnuson, K. M., *Cereal Foods World*, 30:179–181 (1985).
McGuire et al., *J. Econ. Entomol.* 83:2207–2210 (1990).
McGuire et al., *J. Econ. Entomol.* 84:1652–1656 (1991).
McGuire, M. R. and Shasha, B. S., *J. of Econ. Entomol.* 83:1813–1817 (1990).
Meinke et al., *J. Econ. Entomol.* 82:1830–1835 (1989).
Meredith et al., *Cereal Science Today*, 9:33,54 (1964).
Metcalf, R. L. & Lampman, R. L., *J. Econ. Entomol.* 82:1830–1625 (1989).
Rosen et al., *J. Econ. Entomol.* 59:620–622 (1966).
Shasha et al., *J. Appl. Polym. Sci.* 29:67–73 (1984).
Shasha, B. S. & M. R. McGuire. Slow release formulations of pesticides. *In* D. G. Chasin & L. E. Bode, (eds), Pesticide formulations and application systems. American Society for Testing and Materials, Philadelphia (1991).
Shaw et at., *J. Econ. Entomol.* 77:1495–1499 (1984).
Shotwell, R. L., *USDA Tech. Bull.* 793 (1944).
Trimnell et at., *J. of Applied Polymer Science*, 27:3919–3928 (1988).
Trimnell, D. and Shasha, B. S., *J. Controlled Release* 7:263–268 (1988).
Synek, J., Formulation, development, and application of an insecticide granule, pp. 123–131. *In* T. M. Kaneko & N. B. Akesson [eds.] Pesticide formulations and application systems: third symposium, ASTM STP 828. American Society for Testing and Materials, Philadelphia, 1983.
Vander Hooven, D. I. B., Corncob granules and pelleted carriers—new, controlled, safer methods of handling pesticides, pp. 132–140. *In* T. M. Kaneko & N. B. Akesson [eds.] Pesticide formulations and application systems: third symposium, ASTM STP 828. American Society for Testing and Materials, Philadelphia, 1983.
Wall et at., *J. Polymer Sci.*, 24:147–161 (1968).
Wall, J. S. and Beckwith, A. C., *Cereal Science Today*, 14:2455 (1969).
Wall, J. S. and Huebner, F. R., *Protein Functionality in Foods* 147:110–130 (1980).
Weissling, T. J. & Meinke, L. J., *J. Econ. Entomol.* 84:601–609 (1991).
Wing, R. E. and Otey, T. H., *J. Polym. Sci. Polym. Chem. Ed.* 21:121–140 (1983).

What is claimed is:

1. A process for decreasing radiation inactivation of a pest control agent comprising admixing said pest control agent with a protective amount of a gluten, a pH adjuster, and an aqueous solvent to form a sprayable solubilized gluten-based formulation, wherein said formulation has a pH in the range of from about 3.0 to about 5.0 or from about 9.5 to about 12.0, and wherein the amount of gluten is present in a concentration of from about 0.1 grams per 100 milliliters to about 5.0 grams per 100 milliliters.

2. The process according to claim 1, wherein said pest control agent comprises a pesticide.

3. The process according to claim 2, wherein said pesticide is a bacterium, a fungus, a virus, a protozoa or a nematode.

4. The process according to claim 3 wherein said bacterium is *Bacillus thuringiensis*.

5. The process according to claim 2, wherein said pesticide is selected from the group consisting of an insecticide, a herbicide, a fungicide, and a mixture thereof.

6. The process according to claim 5 wherein said insecticide is dimilin, malathion, carbaryl or 0,0-diethyl 0-(6-methyl-2-(1-methylethyl)-4-pyrimidinyl)phosphorothioate.

7. The process according to claim 5 wherein said herbicide is 2,4-D, metolochlor, glyphosate, paraquat or trifluralin.

8. The process according to claim 1 wherein said pest control agent comprises a pest phagostimulant or a pest attractant.

9. The process according to claim 8 wherein said pest attractant is a pheromone.

10. The process according to claim 8 wherein said pest phagostimulant is cucurbitacin.

11. The process according to claim 1 wherein the protective amount of gluten is from about 0.25 grams per 100 milliliters to about 1.5 grams per 100 milliliters of the sprayable gluten-based formulation.

12. The process according to claim 1, wherein the pH is in the range of from about 3.0 to about 5.0.

13. The process according to claim 12, wherein the pH is in the range of from about 3.0 to 3.75.

14. The process according to claim 1, wherein the pH is in the range of from about 9.5 to about 12.

15. The process according to claim 14, wherein the pH is in the range of from about 10 to about 12.

16. The process according to claim 1, wherein the pest control agent is a recombinant *Bacillus thuringiensis* toxin.

17. A process of preparing a sprayable solubilized gluten-based formulation incorporating a pest control agent comprising the steps of:

admixing an effective formulating amount of a gluten, a pesticidally effective amount of said pest control agent, a pH adjuster, and an aqueous solvent;

maintaining said admixture for a period of time sufficient for said admixture to form said sprayable solubilized gluten-based formulation; and recovering said sprayable solubilized gluten-based formulation; wherein said sprayable solubilized gluten-based formulation has a pH in the range of from about 3.0 to about 5.0 or from about 9.5 to about 12.0 and wherein the amount of gluten is present in a concentration of from about 0.1 grams per 100 milliliters to about 5.0 grams per 100 milliliters.

18. The process according to claim 17, wherein the pH is in the range of from about 3.0 to about 5.0.

19. The process according to claim 18, wherein the pH is in the range of from about 3.0 to 3.75.

20. The process according to claim 17, wherein the pH is in the range of from about 9.5 to about 12.

21. The process according to claim 20, wherein the pH is in the range of from about 10 to about 12.

22. The process according to claim 17 wherein the gluten is present in an amount of from about 0.25 grams per 100 milliliters to about 1.5 grams per 100 milliliters.

23. The process of claim 17, wherein said pest control agent is a recombinant *Bacillus thuringiensis* toxin.

* * * * *